(12) United States Patent
Moumene et al.

(10) Patent No.: US 8,641,734 B2
(45) Date of Patent: Feb. 4, 2014

(54) DUAL SPRING POSTERIOR DYNAMIC STABILIZATION DEVICE WITH ELONGATION LIMITING ELASTOMERS

(75) Inventors: Missoum Moumene, Newton, MA (US); Payman Afshari, South Easton, MA (US); Jonathan Fanger, Raynham, MA (US); Kevin Flaherty, Mendon, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 322 days.

(21) Appl. No.: 12/432,141

(22) Filed: Apr. 29, 2009

(65) Prior Publication Data

US 2010/0211104 A1    Aug. 19, 2010

Related U.S. Application Data

(60) Provisional application No. 61/152,610, filed on Feb. 13, 2009.

(51) Int. Cl.
    *A61B 17/70* (2006.01)
(52) U.S. Cl.
    USPC ........... 606/257; 606/246; 606/254; 606/259; 606/264
(58) Field of Classification Search
    USPC .................................. 606/246–279
    See application file for complete search history.

(56) References Cited

U.S. PATENT DOCUMENTS

| | | | |
|---|---|---|---|
| 3,992,725 A | 11/1976 | Homsy | |
| 4,512,038 A | 4/1985 | Alexander | |
| 4,648,388 A * | 3/1987 | Steffee | 606/261 |
| 4,743,260 A | 5/1988 | Burton | |
| 4,854,304 A | 8/1989 | Zielke | |
| 5,002,542 A | 3/1991 | Frigg | |
| 5,034,011 A | 7/1991 | Howland | |
| 5,092,866 A | 3/1992 | Breard | |
| 5,180,393 A | 1/1993 | Commarmond | |
| 5,181,930 A | 1/1993 | Dumbleton | |
| 5,207,678 A | 5/1993 | Harms | |

(Continued)

FOREIGN PATENT DOCUMENTS

| | | |
|---|---|---|
| EP | 46518 | 7/1983 |
| EP | 470660 | 7/1995 |

(Continued)

OTHER PUBLICATIONS

Betz, "Compairson of Anterior and Posterior Instrumentation for Correction of Adolsecent Thoracic Idiipathic Scoliosis", Spine, Feb 1, 1999, vol. 24, Issue 3, pp. 225-239.

(Continued)

*Primary Examiner* — Jerry Cumberledge
*Assistant Examiner* — Nicholas Plionis

(57) ABSTRACT

A Posterior Dynamic Stabilization (PDS) device that regulates physiologic spinal elongation and compression. Regulation of elongation and compression are critical requirements of Posterior Dynamic Stabilization devices. Elongation and compression of the device allow the pedicles to travel naturally as the spine flexes and extends. This interpedicular travel preserves a more natural center of rotation unlike some conventional PDS devices that simply allow bending. The device incorporates two components: 1) a spring that allows elongation/compression, and 2) a polymer core component that serves to increase the stiffness of the device in shear, bending, and tension, and also prevents soft tissue ingrowth.

1 Claim, 11 Drawing Sheets

(56) References Cited

U.S. PATENT DOCUMENTS

| | | |
|---|---|---|
| 5,217,461 A | 6/1993 | Asher |
| 5,217,497 A | 6/1993 | Mehdian |
| 5,282,863 A | 2/1994 | Burton |
| 5,344,422 A | 9/1994 | Frigg |
| 5,360,431 A | 11/1994 | Puno |
| 5,375,823 A | 12/1994 | Navas |
| 5,387,213 A | 2/1995 | Breard |
| 5,403,314 A | 4/1995 | Currier |
| 5,415,661 A | 5/1995 | Holmes |
| 5,423,816 A | 6/1995 | Lin |
| 5,429,639 A | 7/1995 | Judet |
| 5,474,555 A | 12/1995 | Puno |
| 5,486,174 A | 1/1996 | Fournet Fayard |
| 5,496,321 A | 3/1996 | Puno |
| 5,520,689 A | 5/1996 | Schlapfer |
| 5,540,688 A | 7/1996 | Navas |
| 5,540,689 A | 7/1996 | Sanders |
| 5,562,660 A | 10/1996 | Grob |
| 5,562,663 A | 10/1996 | Wisnewski |
| 5,562,737 A | 10/1996 | Graf |
| 5,630,817 A | 5/1997 | Rokegem |
| 5,643,260 A | 7/1997 | Doherty |
| 5,658,286 A | 8/1997 | Sava |
| 5,672,175 A | 9/1997 | Martin |
| 5,672,176 A | 9/1997 | Biederman |
| 5,683,390 A | 11/1997 | Metz Stavenhagen |
| 5,702,395 A | 12/1997 | Hopf |
| 5,704,936 A | 1/1998 | Mazel |
| 5,704,937 A | 1/1998 | Martin |
| 5,728,098 A | 3/1998 | Sherman |
| 5,733,284 A | 3/1998 | Martin |
| 5,738,685 A | 4/1998 | Halm |
| 5,782,833 A | 7/1998 | Haider |
| 5,797,910 A | 8/1998 | Martin |
| 5,851,006 A | 12/1998 | Spillner |
| 5,879,350 A | 3/1999 | Sherman |
| 5,954,725 A | 9/1999 | Sherman |
| 5,961,516 A | 10/1999 | Graf |
| 6,004,349 A | 12/1999 | Jackson |
| 6,022,350 A | 2/2000 | Ganem |
| 6,053,917 A | 4/2000 | Sherman |
| 6,063,090 A | 5/2000 | Schlapfer |
| 6,077,262 A | 6/2000 | Schlapfer |
| 6,083,226 A | 7/2000 | Fiz |
| 6,099,528 A | 8/2000 | Saurat |
| 6,102,912 A | 8/2000 | Cazin |
| 6,139,549 A | 10/2000 | Keller |
| 6,224,598 B1 | 5/2001 | Jackson |
| 6,241,730 B1 | 6/2001 | Alby |
| 6,248,105 B1 | 6/2001 | Schläpfer |
| 6,251,112 B1 | 6/2001 | Jackson |
| 6,267,764 B1 | 7/2001 | Elberg |
| 6,273,888 B1 | 8/2001 | Justis |
| 6,293,949 B1 | 9/2001 | Justis |
| 6,302,888 B1 | 10/2001 | Mellinger |
| 6,361,535 B2 | 3/2002 | Jackson |
| 6,371,957 B1 | 4/2002 | Amrein |
| 6,379,356 B1 | 4/2002 | Jackson |
| 6,402,750 B1 | 6/2002 | Atkinson |
| 6,402,752 B2 | 6/2002 | Schäffler Wachter |
| 6,440,132 B1 | 8/2002 | Jackson |
| 6,471,705 B1 | 10/2002 | Biedermann |
| 6,485,491 B1 | 11/2002 | Farris et al. |
| 6,520,963 B1 | 2/2003 | McKinley |
| 6,540,749 B2 | 4/2003 | Schäfer |
| 6,554,831 B1 | 4/2003 | Rivard |
| 6,595,993 B2 | 7/2003 | Donno |
| 6,626,908 B2 | 9/2003 | Cooper |
| 6,641,586 B2 | 11/2003 | Varieur |
| 6,645,207 B2 | 11/2003 | Dixon |
| 6,652,526 B1 | 11/2003 | Arafiles |
| 6,695,843 B2 | 2/2004 | Biedermann |
| 6,723,100 B2 | 4/2004 | Biedermann |
| 6,726,687 B2 | 4/2004 | Jackson |
| 6,730,089 B2 | 5/2004 | Jackson |
| 6,755,829 B1 | 6/2004 | Bono |
| 6,761,719 B2 | 7/2004 | Justis |
| 6,783,527 B2 | 8/2004 | Drewry |
| 6,786,903 B2 | 9/2004 | Lin |
| 6,796,984 B2 | 9/2004 | Soubeiran |
| 6,835,205 B2 | 12/2004 | Atkinson |
| 6,843,791 B2 | 1/2005 | Serhan |
| 6,896,677 B1 | 5/2005 | Lin |
| 6,905,500 B2 | 6/2005 | Jeon |
| 6,918,911 B2 | 7/2005 | Biedermann |
| 6,966,910 B2 | 11/2005 | Ritland |
| 6,986,771 B2 | 1/2006 | Paul |
| 6,989,011 B2 * | 1/2006 | Paul et al. ............... 606/250 |
| 6,997,927 B2 | 2/2006 | Jackson |
| 7,018,378 B2 | 3/2006 | Biedermann |
| 7,022,122 B2 | 4/2006 | Amrein |
| 7,029,475 B2 | 4/2006 | Panjabi |
| 7,125,410 B2 | 10/2006 | Freudiger |
| 7,137,985 B2 | 11/2006 | Jahng |
| 7,156,850 B2 | 1/2007 | Kim |
| 7,175,622 B2 | 2/2007 | Farris |
| 7,179,261 B2 | 2/2007 | Sicvol |
| 7,204,838 B2 | 4/2007 | Jackson |
| 7,211,086 B2 | 5/2007 | Biedermann |
| 7,261,714 B2 | 8/2007 | Richelsoph |
| 7,326,210 B2 | 2/2008 | Jahng |
| 7,329,258 B2 | 2/2008 | Studer |
| 7,335,200 B2 | 2/2008 | Carli |
| 7,419,714 B1 | 9/2008 | Magerl |
| 7,556,639 B2 | 7/2009 | Rothman |
| 7,621,912 B2 | 11/2009 | Harms |
| 7,621,940 B2 | 11/2009 | Harms |
| 7,632,292 B2 | 12/2009 | Sengupta |
| 7,641,673 B2 | 1/2010 | Le Couedic |
| 7,651,515 B2 | 1/2010 | Mack |
| 7,713,287 B2 | 5/2010 | Timm |
| 7,717,941 B2 | 5/2010 | Petit |
| 7,722,649 B2 | 5/2010 | Biedermann |
| 7,727,258 B2 | 6/2010 | Graf |
| 7,763,052 B2 | 7/2010 | Jahng |
| 7,776,071 B2 | 8/2010 | Fortin |
| 7,776,075 B2 | 8/2010 | Bruneau |
| 7,811,309 B2 | 10/2010 | Timm |
| 7,815,665 B2 | 10/2010 | Jahng |
| 7,833,256 B2 | 11/2010 | Biedermann |
| 7,846,187 B2 | 12/2010 | Jackson |
| 7,862,586 B2 | 1/2011 | Malek |
| 7,942,907 B2 | 5/2011 | Richelsoph |
| 7,988,710 B2 | 8/2011 | Jahng |
| 7,993,370 B2 | 8/2011 | Jahng |
| 8,012,178 B2 | 9/2011 | Hartmann |
| 8,241,362 B2 | 8/2012 | Voorhies |
| 2002/0058942 A1 | 5/2002 | Biedermann |
| 2002/0072751 A1 | 6/2002 | Jackson |
| 2002/0082602 A1 | 6/2002 | Biedermann |
| 2002/0133155 A1 | 9/2002 | Ferree |
| 2002/0133159 A1 | 9/2002 | Jackson |
| 2003/0009226 A1 | 1/2003 | Graf |
| 2003/0041441 A1 | 3/2003 | Lin |
| 2003/0055426 A1 | 3/2003 | Carbone |
| 2003/0055427 A1 | 3/2003 | Graf |
| 2003/0083657 A1 | 5/2003 | Drewry |
| 2003/0100896 A1 | 5/2003 | Biedermann |
| 2003/0109880 A1 | 6/2003 | Shirado |
| 2003/0125741 A1 | 7/2003 | Biedermann |
| 2003/0149431 A1 | 8/2003 | Varieur |
| 2003/0153912 A1 | 8/2003 | Graf |
| 2003/0171749 A1 | 9/2003 | Le Couedic |
| 2003/0191470 A1 | 10/2003 | Ritland |
| 2003/0220642 A1 | 11/2003 | Freudiger |
| 2003/0220643 A1 | 11/2003 | Ferree |
| 2004/0002708 A1 | 1/2004 | Ritland |
| 2004/0049189 A1 | 3/2004 | Le Couedic |
| 2004/0049190 A1 | 3/2004 | Biedermann |
| 2004/0068258 A1 | 4/2004 | Schlapfer |
| 2004/0073215 A1 | 4/2004 | Carli |
| 2004/0097926 A1 | 5/2004 | Kim |
| 2004/0097933 A1 | 5/2004 | Lourdel |
| 2004/0106921 A1 | 6/2004 | Cheung |

(56) References Cited

U.S. PATENT DOCUMENTS

| | | |
|---|---|---|
| 2004/0116927 A1 | 6/2004 | Graf |
| 2004/0143264 A1 | 7/2004 | McAfee |
| 2004/0167523 A1 | 8/2004 | Jackson |
| 2004/0186474 A1 | 9/2004 | Matthis |
| 2004/0186478 A1 | 9/2004 | Jackson |
| 2004/0215191 A1 | 10/2004 | Kitchen |
| 2004/0215192 A1 | 10/2004 | Justis |
| 2004/0225289 A1 | 11/2004 | Biedermann |
| 2004/0230191 A1 | 11/2004 | Frey |
| 2004/0230192 A1 | 11/2004 | Graf |
| 2004/0236327 A1 | 11/2004 | Paul |
| 2004/0236328 A1 | 11/2004 | Paul |
| 2004/0236329 A1 | 11/2004 | Panjabi |
| 2004/0260284 A1 | 12/2004 | Parker |
| 2004/0264386 A1 | 12/2004 | Ha |
| 2004/0267260 A1 | 12/2004 | Mack |
| 2005/0027292 A1 | 2/2005 | Bernard |
| 2005/0033295 A1 | 2/2005 | Wisnewski |
| 2005/0038432 A1 | 2/2005 | Shaolian |
| 2005/0049708 A1 | 3/2005 | Atkinson |
| 2005/0056979 A1 | 3/2005 | Studer |
| 2005/0065514 A1 | 3/2005 | Studer |
| 2005/0065516 A1 | 3/2005 | Jahng |
| 2005/0080414 A1 | 4/2005 | Keyer |
| 2005/0085814 A1 | 4/2005 | Sherman |
| 2005/0085815 A1 | 4/2005 | Harms |
| 2005/0113927 A1 | 5/2005 | Malek |
| 2005/0124991 A1 | 6/2005 | Jahng |
| 2005/0129499 A1 | 6/2005 | Morris |
| 2005/0131407 A1 | 6/2005 | Sicvol |
| 2005/0131421 A1 | 6/2005 | Anderson |
| 2005/0131422 A1 | 6/2005 | Anderson |
| 2005/0143737 A1 | 6/2005 | Pafford |
| 2005/0143823 A1 | 6/2005 | Boyd |
| 2005/0149020 A1 | 7/2005 | Jahng |
| 2005/0154389 A1 | 7/2005 | Selover |
| 2005/0154390 A1 | 7/2005 | Biedermann |
| 2005/0165396 A1 | 7/2005 | Fortin |
| 2005/0171543 A1 | 8/2005 | Timm |
| 2005/0177156 A1 | 8/2005 | Timm |
| 2005/0177157 A1 | 8/2005 | Jahng |
| 2005/0177164 A1 | 8/2005 | Walters |
| 2005/0182400 A1 | 8/2005 | White |
| 2005/0182401 A1 | 8/2005 | Timm |
| 2005/0182409 A1 | 8/2005 | Callahan |
| 2005/0187549 A1 | 8/2005 | Jackson |
| 2005/0192589 A1 | 9/2005 | Raymond |
| 2005/0202519 A1 | 9/2005 | Barthe |
| 2005/0203511 A1 | 9/2005 | Wilson MacDonald |
| 2005/0203513 A1 | 9/2005 | Jahng |
| 2005/0203514 A1 | 9/2005 | Jahng |
| 2005/0203516 A1 | 9/2005 | Biedermann |
| 2005/0203517 A1 | 9/2005 | Jahng |
| 2005/0203518 A1 | 9/2005 | Biedermann |
| 2005/0203519 A1 | 9/2005 | Harms |
| 2005/0215999 A1 | 9/2005 | Birkmeyer |
| 2005/0216003 A1 | 9/2005 | Biedermann |
| 2005/0222569 A1 | 10/2005 | Panjabi |
| 2005/0222659 A1 | 10/2005 | Olsen |
| 2005/0245930 A1 | 11/2005 | Timm |
| 2005/0261685 A1 | 11/2005 | Fortin |
| 2005/0261686 A1 | 11/2005 | Paul |
| 2005/0267471 A1 | 12/2005 | Biedermann |
| 2005/0277919 A1 | 12/2005 | Slivka |
| 2005/0277922 A1 | 12/2005 | Trieu |
| 2005/0288670 A1 | 12/2005 | Panjabi |
| 2005/0288672 A1 | 12/2005 | Ferree |
| 2006/0009768 A1 | 1/2006 | Ritland |
| 2006/0014259 A9 | 1/2006 | Burke |
| 2006/0025767 A1 | 2/2006 | Khalili |
| 2006/0036240 A1 | 2/2006 | Colleran |
| 2006/0041259 A1 | 2/2006 | Paul |
| 2006/0064090 A1 | 3/2006 | Park |
| 2006/0084984 A1* | 4/2006 | Kim .................. 606/61 |
| 2006/0106380 A1 | 5/2006 | Colleran |
| 2006/0106381 A1 | 5/2006 | Ferree |
| 2006/0129147 A1* | 6/2006 | Biedermann et al. .......... 606/61 |
| 2006/0142758 A1* | 6/2006 | Petit ............... 606/61 |
| 2006/0142760 A1 | 6/2006 | McDonnell |
| 2006/0149235 A1 | 7/2006 | Jackson |
| 2006/0149291 A1 | 7/2006 | Selover |
| 2006/0155279 A1 | 7/2006 | Ogilvie |
| 2006/0161152 A1 | 7/2006 | Ensign |
| 2006/0184171 A1 | 8/2006 | Biedermann |
| 2006/0189983 A1 | 8/2006 | Fallin |
| 2006/0189984 A1 | 8/2006 | Fallin |
| 2006/0195093 A1 | 8/2006 | Jahng |
| 2006/0212033 A1 | 9/2006 | Rothman |
| 2006/0229607 A1 | 10/2006 | Brumfield |
| 2006/0229608 A1 | 10/2006 | Foster |
| 2006/0229612 A1* | 10/2006 | Rothman et al. ................. 606/61 |
| 2006/0240533 A1* | 10/2006 | Sengupta et al. ............. 435/117 |
| 2006/0247632 A1 | 11/2006 | Winslow |
| 2006/0247637 A1 | 11/2006 | Colleran |
| 2006/0260483 A1 | 11/2006 | Hartmann |
| 2006/0264935 A1 | 11/2006 | White |
| 2006/0264937 A1 | 11/2006 | White |
| 2006/0265074 A1 | 11/2006 | Krishna |
| 2006/0282080 A1 | 12/2006 | Albert |
| 2007/0003598 A1 | 1/2007 | Trieu |
| 2007/0005063 A1 | 1/2007 | Bruneau |
| 2007/0016190 A1 | 1/2007 | Martinez |
| 2007/0016201 A1 | 1/2007 | Freudiger |
| 2007/0019808 A1 | 1/2007 | Gonzalez |
| 2007/0049937 A1* | 3/2007 | Matthis et al. .................. 606/61 |
| 2007/0055241 A1 | 3/2007 | Matthis |
| 2007/0055244 A1 | 3/2007 | Jackson |
| 2007/0055247 A1 | 3/2007 | Jahng |
| 2007/0161992 A1 | 7/2007 | Kwak |
| 2007/0191832 A1 | 8/2007 | Trieu |
| 2007/0191841 A1 | 8/2007 | Justis |
| 2007/0198088 A1 | 8/2007 | Biedermann |
| 2007/0233064 A1 | 10/2007 | Holt |
| 2007/0233073 A1 | 10/2007 | Wisnewski |
| 2007/0233085 A1 | 10/2007 | Biedermann |
| 2007/0233097 A1 | 10/2007 | Anderson |
| 2007/0270814 A1* | 11/2007 | Lim et al. .......... 606/61 |
| 2007/0270838 A1 | 11/2007 | Bruneau |
| 2008/0021469 A1 | 1/2008 | Holt |
| 2008/0033435 A1 | 2/2008 | Studer |
| 2008/0058809 A1 | 3/2008 | Graf |
| 2008/0140133 A1 | 6/2008 | Allard |
| 2008/0147122 A1 | 6/2008 | Jackson |
| 2008/0161853 A1 | 7/2008 | Arnold |
| 2008/0161863 A1 | 7/2008 | Arnold |
| 2008/0183213 A1 | 7/2008 | Veldman |
| 2008/0195105 A1* | 8/2008 | Sidebotham et al. ........... 606/80 |
| 2008/0195153 A1 | 8/2008 | Thompson |
| 2008/0262552 A1 | 10/2008 | Kim |
| 2008/0312694 A1 | 12/2008 | Peterman |
| 2009/0005817 A1 | 1/2009 | Friedrich |
| 2009/0012562 A1 | 1/2009 | Hestad |
| 2009/0030464 A1 | 1/2009 | Hestad |
| 2009/0048631 A1* | 2/2009 | Bhatnagar et al. ............. 606/246 |
| 2009/0062866 A1 | 3/2009 | Jackson |
| 2009/0099608 A1* | 4/2009 | Szczesny ..................... 606/257 |
| 2009/0131981 A1 | 5/2009 | White |
| 2009/0163953 A1 | 6/2009 | Biedermann |
| 2009/0204155 A1 | 8/2009 | Aschmann |
| 2009/0251573 A1 | 10/2009 | Toyoda |
| 2009/0281573 A1* | 11/2009 | Biedermann et al. ......... 606/257 |
| 2010/0042156 A1 | 2/2010 | Harms |
| 2010/0069962 A1 | 3/2010 | Harms |
| 2010/0069964 A1 | 3/2010 | Lechmann |
| 2010/0114169 A1 | 5/2010 | Le Couedic |
| 2010/0114173 A1 | 5/2010 | Le Couedic |
| 2010/0174317 A1 | 7/2010 | Timm |
| 2010/0204736 A1 | 8/2010 | Biedermann |
| 2011/0054534 A1 | 3/2011 | Biedermann |

FOREIGN PATENT DOCUMENTS

| | | |
|---|---|---|
| EP | 667127 | 8/1995 |
| EP | 516567 | 7/1997 |

(56) References Cited

FOREIGN PATENT DOCUMENTS

| | | |
|---|---|---|
| EP | 669109 | 5/1999 |
| EP | 732081 | 5/2000 |
| EP | 1281364 | 1/2004 |
| EP | 1364622 | 7/2005 |
| EP | 1579816 | 9/2005 |
| EP | 1388323 | 1/2007 |
| EP | 1574173 | 1/2007 |
| EP | 1523949 | 6/2007 |
| EP | 1747760 | 10/2009 |
| EP | 1488751 | 11/2009 |
| EP | 1586276 | 11/2009 |
| EP | 1776927 | 9/2010 |
| EP | 1658815 | 3/2012 |
| FR | 2717370 | 9/1995 |
| GB | 2382307 | 5/2003 |
| JP | 2004073855 | 3/2004 |
| JP | 2005118569 | 5/2005 |
| WO | 9501132 | 1/1995 |
| WO | 9505783 | 3/1995 |
| WO | 9513755 | 5/1995 |
| WO | 9641582 | 12/1996 |
| WO | 0145576 | 6/2001 |
| WO | 0156489 | 8/2001 |
| WO | 0207622 | 1/2002 |
| WO | 0217803 | 4/2002 |
| WO | 0243603 | 6/2002 |
| WO | 0269854 | 9/2002 |
| WO | 03007828 | 1/2003 |
| WO | 03009737 | 2/2003 |
| WO | 0212259 A3 | 5/2003 |
| WO | 03041441 | 5/2003 |
| WO | 03041599 | 5/2003 |
| WO | 03047441 | 6/2003 |
| WO | 2004024011 | 3/2004 |
| WO | 2004034916 | 4/2004 |
| WO | 2004064653 | 8/2004 |
| WO | 2005027761 | 3/2005 |
| WO | 2005030066 | 4/2005 |
| WO | 2005039454 | 7/2005 |
| WO | 2005013839 | 8/2005 |
| WO | 2005044117 | 8/2005 |
| WO | 2005094704 | 10/2005 |
| WO | 2005030031 | 1/2006 |
| WO | 2006066053 | 6/2006 |
| WO | 2006118866 | 11/2006 |
| WO | 2006063107 | 12/2006 |
| WO | 2007007545 | 1/2007 |
| WO | 2006116437 | 2/2007 |
| WO | 2006115539 | 5/2007 |
| WO | 2008003047 | 6/2008 |

OTHER PUBLICATIONS

Desroches "Biomechanical modeling of anterior spine instrumentation in AIS", Stud Health Technol Inform, 2006, vol. 123, pp. 415-418—abstract.

Hefti, "Repair of lumbar spondylolysis with a hook-screw", Int Orthop., 1992, vol. 16, Issue 1, pp. 81-85—abstract.

Nohara, "Biomechanical study of adjacent intervertebral motion after lumbar spinal fusion and flexible stabilization using polyethylene-terephthalate bands", J Spinal Discord Tech, Jun. 2004, vol. 17, Issue 3, pp. 215-219—abstract.

Poulin, "Biomechanical modeling of instrumentation for the scoliotic spine using flexible elements: a feasibility study", Ann Chir, 1998, 52(8), pp. 761-767—abstract.

Sanders, "A Preliminary Investigation of Shape Memory Alloys in the Surgical Correction of Scoliosis", Spine, Sep. 15, 1993, vol. 18, Issue 12, pp. 1640-1646.

Smith, "Does Instrumented Anterior Scoliosis Surgery Lead to Pyphosis, Pseudarthrosis, or Inadequate Correction in Adults", Spine, Mar. 1, 2002, vol. 27, Issue 5, pp. 529-34.

Teitelbaum, "New Percutaneously Inserted Spinal Fixation System", Spine, Mar. 11, 2004, vol. 29, Issue 6, pp. 703-709.

Veldhuizen, "A Scoliosis Correction Device Based on Memory Metal", Med. Eng. Phys., 1997, vol. 19, pp. 171-179, Elsevier Science Ltd.

\* cited by examiner

DUAL SPRING POSTERIOR DYNAMIC STABILIZATION DEVICE WITH ELONGATION LIMITING ELASTOMERS

CONTINUING DATA

This non-provisional patent application claims priority from provisional U.S. Ser. No. 61/152,610, filed Feb. 13, 2009, entitled "Dual Spring Rod with Elongation Limiting Elastomer" (Moumene).

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. One drawback of current articulating facet replacement devices, however, is that they require the facet joints to be resected. Moreover, alignment of the articulating surfaces with one another can be challenging.

Accordingly, there remains a need for improved systems and methods that are adapted to mimic the natural function of the facet joints.

US Patent Publication No. 2006/0142758 ("Petit") discloses a linking element that consists of a helical spring and a support member made out of a polymer material. The helical spring is embedded in the support material.

US Patent Publication No. 2004/0215191 ("Kitchen") discloses a flexible tube comprising at least one lumen that extends the length of the tube. At least one rod of a preformed curvature is present within said one lumen of the tube. As additional rods are placed within the hollow flexible member, increased force is applied to the spine by the device, thereby moving the spine towards the desired curvature.

US Patent Publication No. 2004/0049189 ("Le Couedic") discloses a device that has two rigid rod-forming parts made of a first material. A connecting body that is made entirely from a second material that is more elastically deformable than said first material interconnects the two rod-forming portions.

US Patent Publication No. 2005/0065514 ("Studer") discloses a dampening element comprising two spring elements coaxial with or parallel to a longitudinal axis, and two axially end-side connectors. The end-side connectors can be linked to the spring elements such that at least one of the spring elements is connected to the connectors. The two spring elements have different spring rates and one sprint element is designed as a tension and compression spring and comprises a spring coil, and the damping element is pre-stressed.

EP Patent Publication No. 0 677 277 ("Moreau I") discloses a helically split oblong rotating member attached to upper and lower parts. The hollow central part of said member is filled at rest with a viscoelastic cushioning product cast in inter-thread overflow.

FR Patent Publication No. 2 717 370 ("Moreau II") discloses an intervertebral stabilizing prosthesis comprising a hollow body of revolution that is radially and/or helically slotted to make it axially flexible, whose internal spaces and slots are filled with a viscoelastic product constituting an elastic shock-absorbing tensioner that is micrometrically adjustable. Yoke systems allow the assembly to be embedded by nuts into anchors and screwed into the bone.

GB Patent Publication No. 2 382 307 ("Sengupta") discloses an assembly for soft stabilization of the spine comprising a pair of pedicle screws and a helical spring member. The helical spring member may be made from titanium or stainless steel. A plastic sleeve may or may not cover the spring.

US Patent Publication No. 2005/0203517 ("Jahng") discloses an elastomer cladding on a wire.

U.S. Pat. No. 6,989,011 (Paul) discloses a device containing a spring and two ends, where the ends and the spring are integrally formed.

US 2006/0041259 (Paul) discloses a dynamic device containing at least one spring integrally formed to the substantially solid ends.

US 2003/0109880 (Shirado) discloses a resilient PDS member with anchors.

U.S. Pat. No. 6,761,719 (Justis) discloses a device for stabilizing at least a portion of the spinal column, including a longitudinal member sized to span a distance between at least two vertebral bodies and being at least partially formed of a shape-memory material exhibiting pseudoelastic characteristics at about human body temperature. A number of bone anchors are used to secure the longitudinal member to each of the vertebral bodies. The longitudinal member is reformed from an initial configuration to a different configuration in response to the imposition of stress caused by relative displacement between the vertebral bodies, and recovers toward the initial configuration when the stress is removed to thereby provide flexible stabilization to the spinal column. During reformation of the longitudinal member, at least a portion of the shape-memory material transforms into stress-induced martensite. In a particular aspect of the invention, the longitudinal member is a plate having a central portion at least partially formed of the shape-memory material, and a pair of connection portions disposed at opposite ends of the central portion for connection to each of the vertebral bodies. The central portion of the plate defines a number of alternating ridges and grooves along a length thereof having an initial amplitude corresponding to the initial configuration and a different amplitude corresponding to the different configuration.

US 2004/0236329 (Panjabi) discloses a dynamic rod device with greater resistance to movement during the central zone and lower resistance to movement as it extends beyond the central zone, i.e. neutral zone theory.

US 2005/0171543 (Timm) discloses a pedicle based dynamic stabilization system.

US 2006/0036240 (Colleran) discloses a dynamic device allowing controlled motion and disc off loading.

US 2008/0033435 (Studer) discloses a dynamic device with two springs and a dampening element where the two springs have different spring constants.

US 2006/0282080 (Albert) discloses a dynamic device with a spring element.

SUMMARY OF THE INVENTION

The present invention provides a Posterior Dynamic Stabilization (PDS) device that regulates physiologic spinal elongation and compression. Regulation of elongation and compression are critical requirements of Posterior Dynamic Stabilization devices. Elongation and compression of the device allow the pedicles to travel naturally as the spine flexes and extends. This interpedicular travel preserves a more natural center of rotation unlike some conventional PDS devices that simply allow bending. The present invention incorporates two components: 1) a spring that allows elongation/compression, and 2) a polymer core component that serves to increase the stiffness of the device in shear, bending, and tension, and also prevents soft tissue ingrowth.

Preferred embodiments of the device of the present invention feature a single-level device used for Posterior Dynamic Stabilization that comprises a dual-helix titanium spring, a polymer core component disposed within the spring, and a pair of bone anchor attachment features.

The dual helix spring has numerous parameters that can be altered to adjust the overall device stiffness, and which may include: wire diameter, spring overall diameter, spring pitch and material of construction. The spring can take many forms that allow it to be linked to a bone anchor. The preferred embodiment of the invention includes a coiled spring whose ends terminate in linear sections running substantially parallel to the axis of the spring coil. This, however, is not a requirement and the coil could terminate in any means that can attach to a bone anchor.

The polymer core component regulates the response of the spring by limiting its elongation. The polymer component also has numerous parameters that can be altered to adjust the overall device stiffness, which may include: clearance of polymer core with inner diameter of spring, length, and material of construction. In a preferred embodiment, the polymer component fills the inner diameter of the spring. However, this component could take many forms.

The attachment feature allows the spring component of the device to attach to a bone anchor. An attachment feature is typically located at each end of the device and together they flank the centrally located spring. The attachment feature can be integral to the spring or it can be a separate component that allows it to mate to bone anchors such as a screw or a hook. In some embodiments, the attachment feature is a rod, preferably having an open bore opening from its inner end.

Therefore, in accordance with the present invention, there is provided a posterior dynamic stabilization device comprising;

a) a first end attachment feature adapted for attachment to a first bone anchor,
b) a second end attachment feature adapted for attachment to a second bone anchor,
c) an intermediate spring portion comprising first and second springs, each spring having a helical intermediate portion, the helical intermediate portions oriented to form a double helix.

Preferably, the double helix defines an internal space and the device further comprises:

d) a polymer core located at least within the internal space of the double helix.

DETAILED DESCRIPTION OF THE INVENTION

Figure 1:
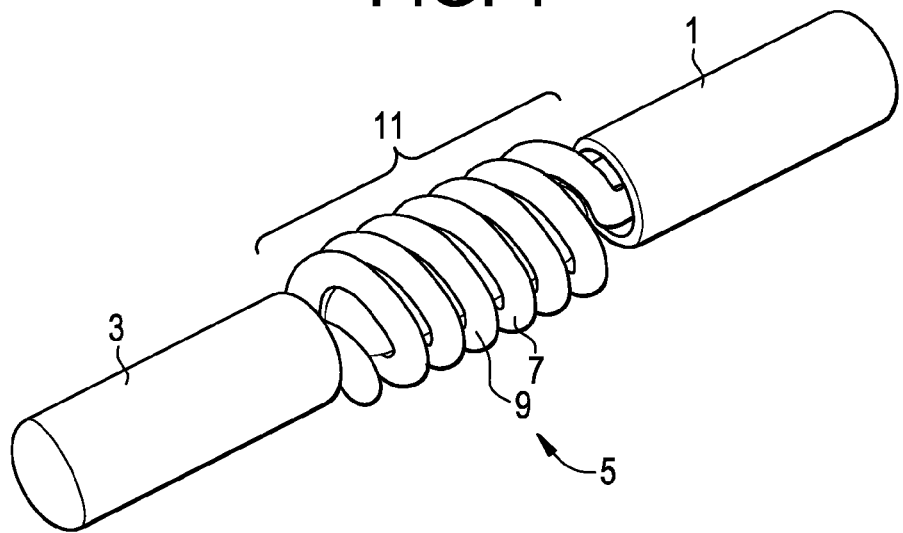
FIG. 1 discloses a first embodiment of the device of the present invention.

Now referring to FIG. 1, there is provided a posterior dynamic stabilization device comprising;

a) a first end attachment feature 1 adapted for attachment to a first bone anchor,
b) a second end attachment feature 3 adapted for attachment to a second bone anchor, and
c) an intermediate spring portion 5 comprising a first spring 7 and a second spring 9, each spring having a helical intermediate portion 11, the helical intermediate portions oriented to form a double helix.

Figure 2:
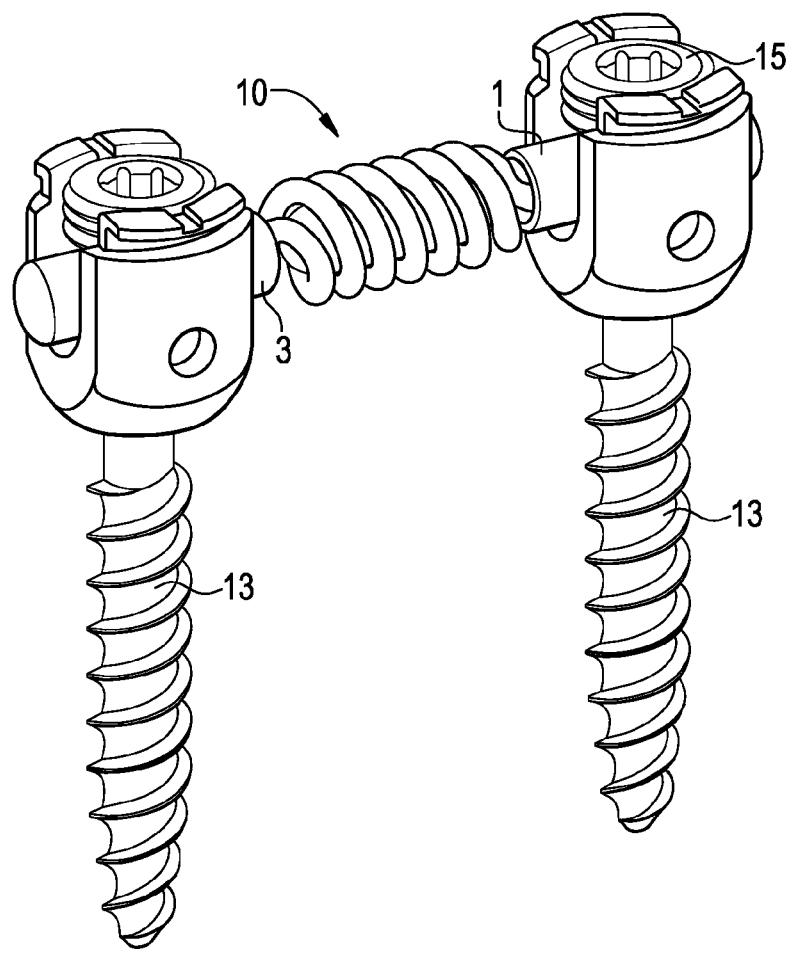
FIG. 2 discloses the device of FIG. 1 attached to a pair of bone anchors.
Figure 3:
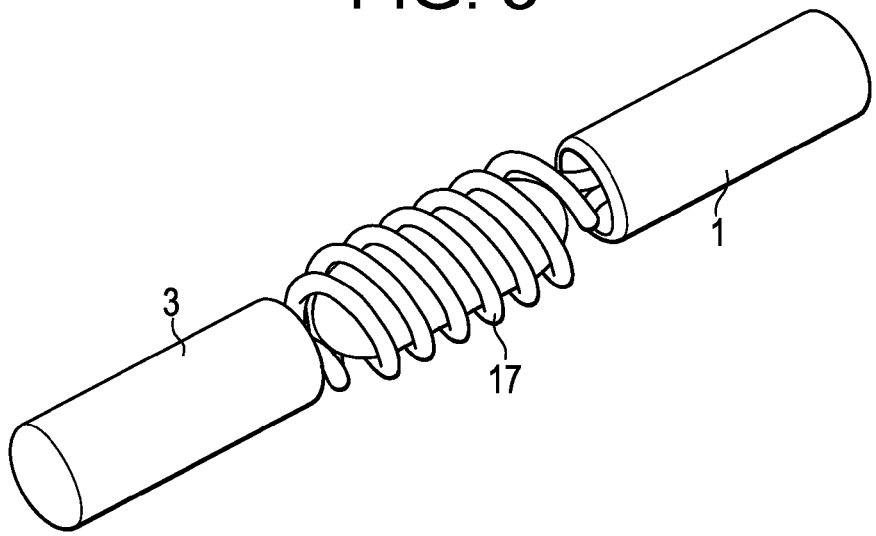
FIG. 3 discloses the device of FIG. 1 modified with a smaller diameter wire in the spring section.

Now referring to FIGS. 2-3, there is provided a single level device 10 of the present invention, wherein the device is attached to two bone anchors 13 by securing a set screw 15 to the respective attachment feature portions 1,3 of the device. As stated above, various parameters of the device's spring may be changed to modify and alter its stiffness. In this FIG.

3, a smaller wire diameter on the springs 17 is shown. This feature may be combined with other alterations (such as overall diameter of the spring, material, etc) to alter device performance. In this case, the smaller wire diameter decreases the stiffness of the spring (and thus the device). In some embodiments, a kit is provided with various spring geometries and/or with various polymer properties to create a spectrum of rod stiffnesses that can be selected by the surgeon to treat a variety of surgical indications.

Figure 4A:
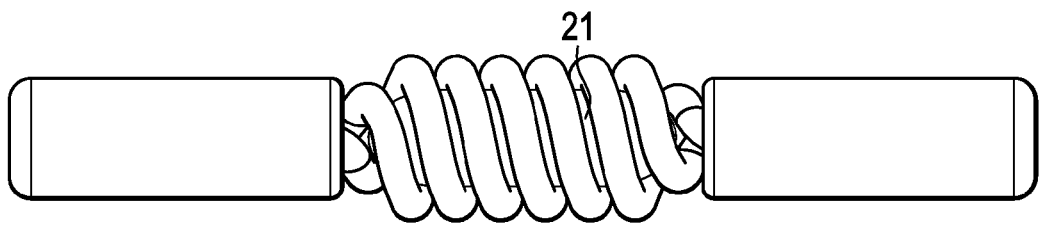
FIGS. 4a-b disclose side and cross-section views of the device of FIG. 1.
Figure 4B:
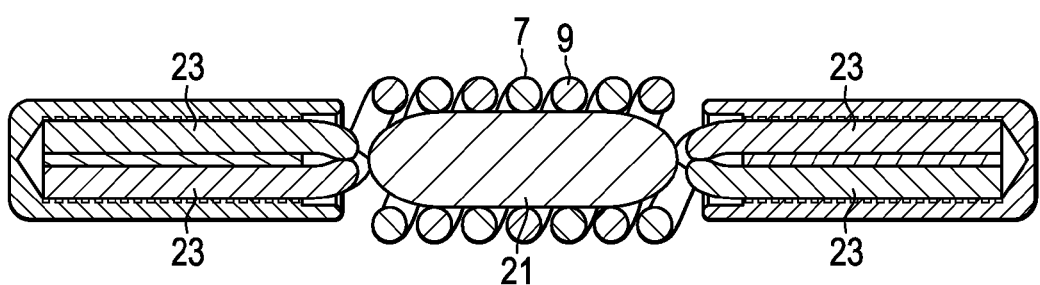

Now referring to FIGS. 4a-4b, the polymer component 21 of the device offers some resistance to device elongation as the spring stretches during physiologic spinal elongation and squeezes the polymer core. Therefore, the polymer component contributes to device performance by helping control both elongation and compression of the spring unit.

As shown best in FIG. 4b, in some embodiments, the ends 23 of the springs 7,9 are contained within the respective opposing attachment features (in this case, the rods). This containment may be accomplished in a variety of ways. The dual spring ends may also be captured within attachment features that possess geometries other than a rod geometry (such as a square or a block).

Figure 5:
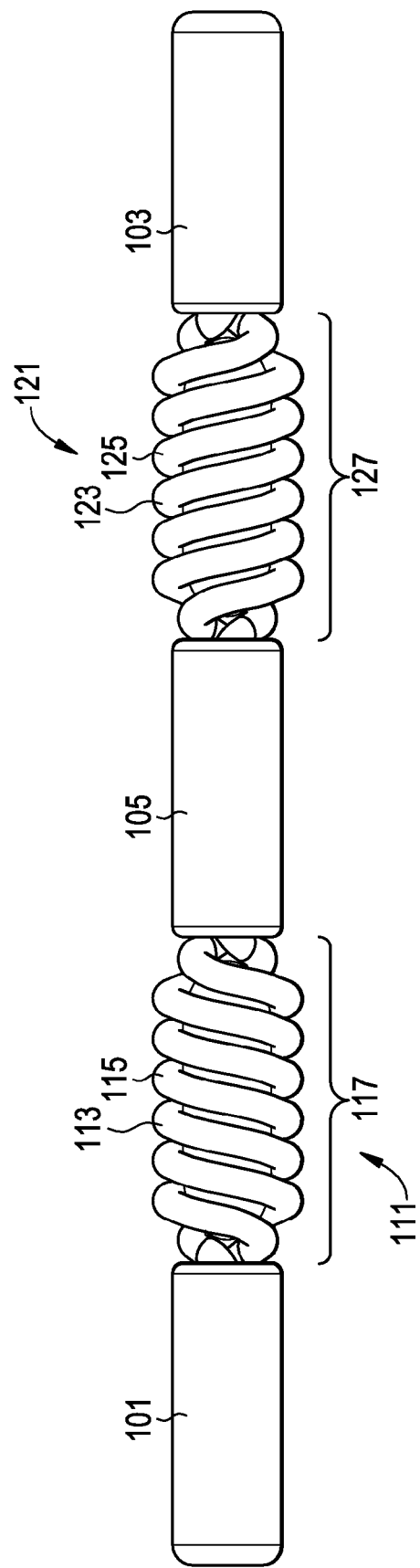
FIG. 5 discloses a multi-level embodiment of the device of the present invention.

Now referring to FIG. 5, multi-level devices of the present invention can be constructed in a variety of configurations by using two or more spring sections. The stiffness at each segment may be the same or it may vary depending on the indication being treated.

Therefore, in accordance with the present invention, there is provided a multi-level posterior dynamic stabilization device comprising;
a) a first end attachment feature 101 adapted for attachment to a first bone anchor,
b) a second end attachment feature 103 adapted for attachment to a second bone anchor,
c) an intermediate attachment feature 105 adapted for attachment to a third bone anchor
d) a first intermediate spring portion 111 located between the first end attachment feature and the intermediate attachment feature, and comprising a first spring 113 and a second spring 115, each spring having a helical intermediate portion 117, the helical intermediate portions oriented to form a first double helix, and
e) a second intermediate spring portion 121 located between the second end attachment feature and the intermediate attachment feature, and comprising a third spring 123 and a fourth spring 125, each spring having a helical intermediate portion 127, the helical intermediate portions oriented to form a second double helix.

Figure 6:
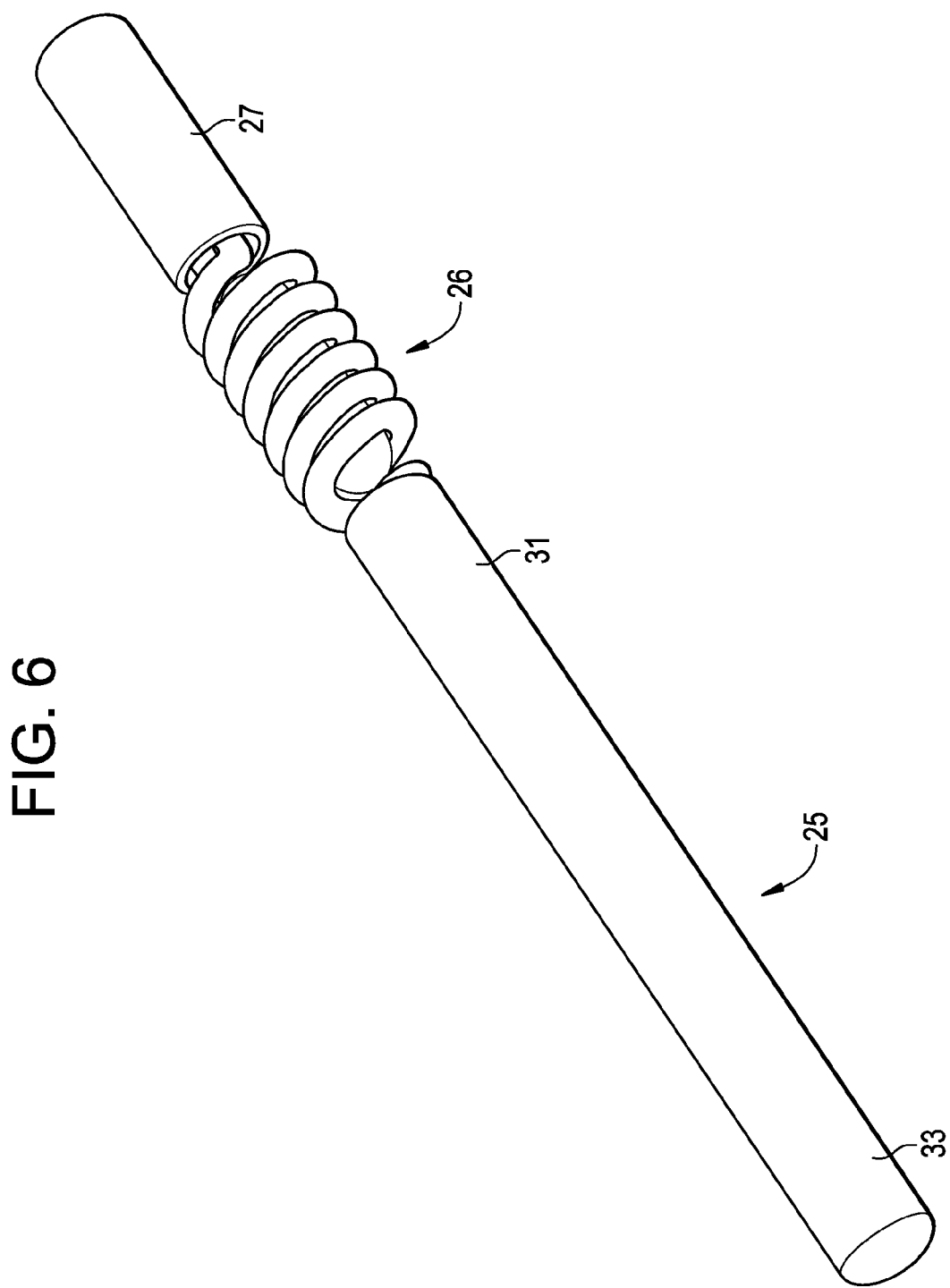
FIG. 6 discloses a device of the present invention preferably used for topping off.

Now referring to FIG. 6, another embodiment of the present invention features a first long rod 25 and a short rod segment 27 attached to a central spring 26. This embodiment may be used to address cases in which the surgeon would like to "top off" a fusion. In use, both short rod 27 and the inner portion 31 of the long rod are attached to bone anchors at the terminating level of the construct. The outer portion 33 of the long rod is attached to a bone anchor at a fusion segment. Therefore, in accordance with the present invention, there is provided the device of the present invention wherein the first rod has a first length and the second rod has a second length, wherein the first length is greater than the second length. Preferably, the first length is at least two times greater than the second length.

As mentioned above, various components of this device can be modified to achieve a desired profile of stiffnesses in tension, shear, and bending. Now referring to FIGS. 7 and 8, a second polymer component 35 is molded entirely around the central spring portions. Addition of this "overmolded" polymer component increases the stiffness of the device. This "overmolded" polymer component is further advantageous because it also prevents tissue in-growth, thereby preventing tissue from entering the springs when the spine moves and the springs stretch.

Figure 7:
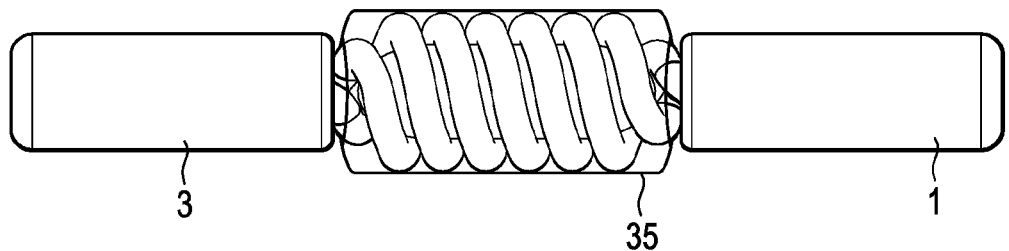
FIG. 7 discloses the device of FIG. 1 in which the spring unit is overmolded with a second polymer component.
Figure 8:
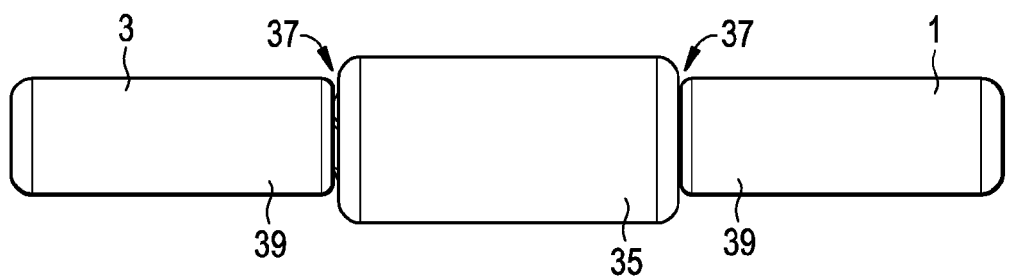
FIG. 8 discloses the device of FIG. 7 in which gaps are present between the attachment end features and the central overmolded polymer component.
Figure 9:
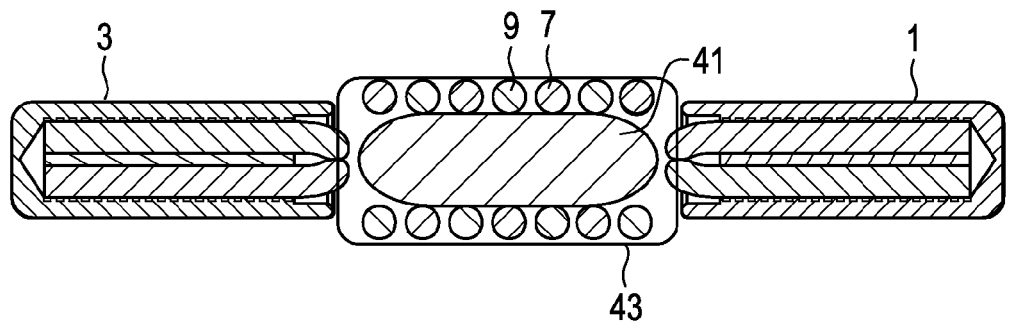
FIG. 9 discloses a cross-section of FIG. 8.

Therefore, and now referring to FIGS. 7-9, in some embodiments, a first polymer core 41 is located within the internal space of the double helix and a second polymer component 35 extends through the double helix to overmold the helix. In some embodiments, the first and second polymer components are integral. In some embodiments, the overmolding extends to only tangentially cover the helix. In other embodiments, the overmolding extends past the helix.

Now referring to FIG. 8, the device may include a gap 37 present as a space between the overmolded polymer component 35 and the inner ends 39 of the rod/anchor attachment portion. Therefore, in some embodiments, the first end attachment feature comprises a first rod, and the second end attachment feature comprises a second rod, and wherein the polymer core and the first rod define a first gap therebetween, and wherein the polymer core and the second rod define a second gap therebetween. The function of the gap is to prevent molding of the rod.

Now referring to FIG. 9, the polymer component can be constructed as a single integral component or as a plurality of separate components. In one embodiment, the polymer core 41 is assembled and a separate outer polymer sheath 43 is either overmolded or assembled. The core and outer sheath may also be manufactured as one integral component using an overmold process.

Therefore, in some embodiments, the polymer core is located within the internal space of the double helix and extends through the double helix to overmold the helix.

The polymer component may be selected from a range of polymers with a range of durometers and stiffnesses. The polymer may be elastomer-based, thermoplastic-based, or may be a composite of the two. In preferred embodiments, the polymer component is selected from silicone rubber or polycarbonate urethane.

Figure 10:
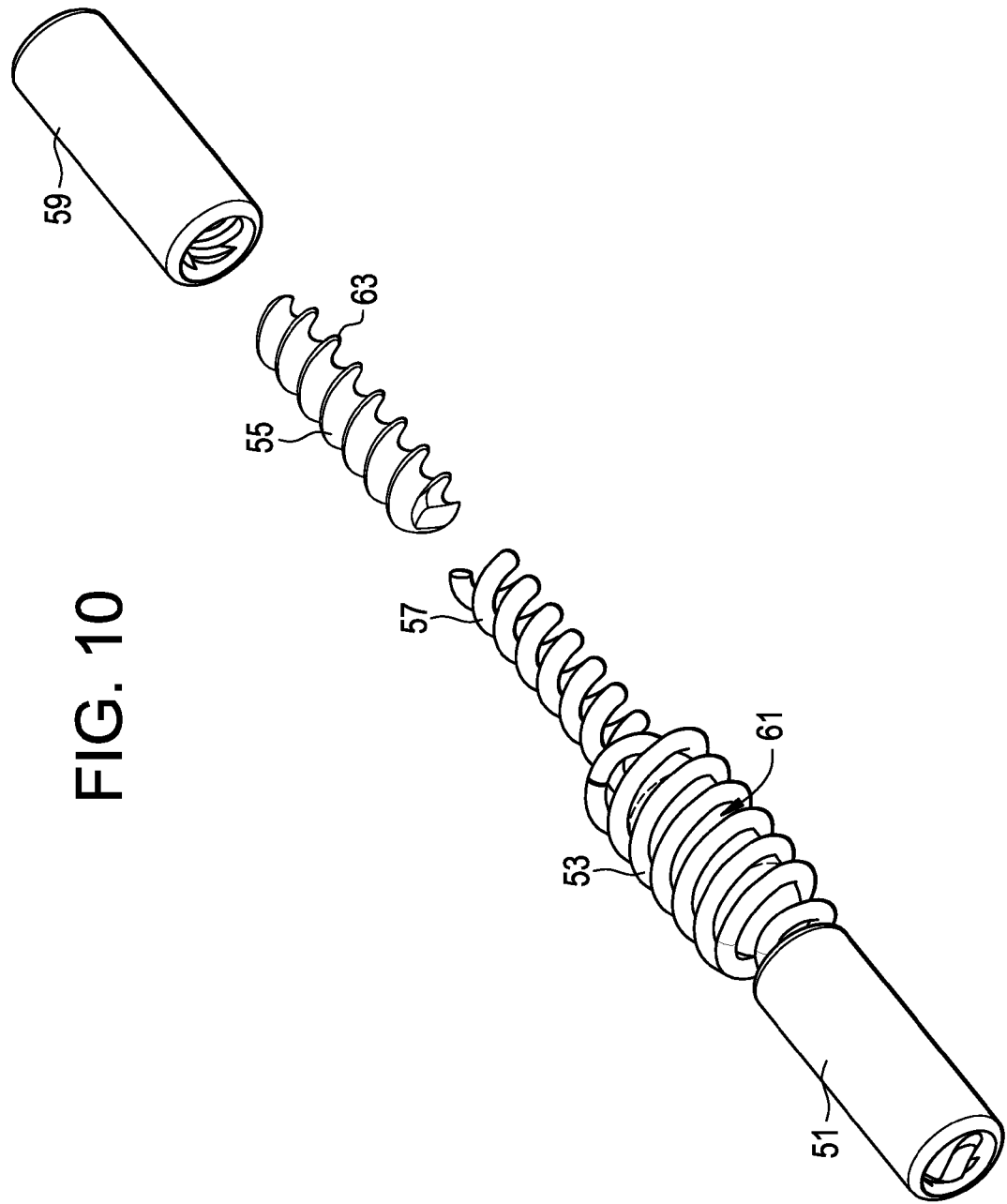
FIG. 10 discloses an exploded view of an embodiment of the present invention having a solid component inserted into a spring end.

There are many possible configurations leading to assembly of the device. In one manufacturing method, and now referring to FIG. 10, a first tube 51 is threaded over the dual spring 53 to provide a clamping surface. A solid component 55 is then threaded into terminating end 57 of the spring to prevent collapse and allow attachment to the clamping end tube 59. The polymer core 61 may be passed through the tighter terminating end of coil in multiple pieces.

Therefore, in accordance with the present invention, in one embodiment, each spring further comprises a first spring termination end 57 having a first diameter, and the device further comprises d) a solid component 55 having a threaded outer surface 63, wherein the solid component is located within the first spring termination end.

Figure 11:
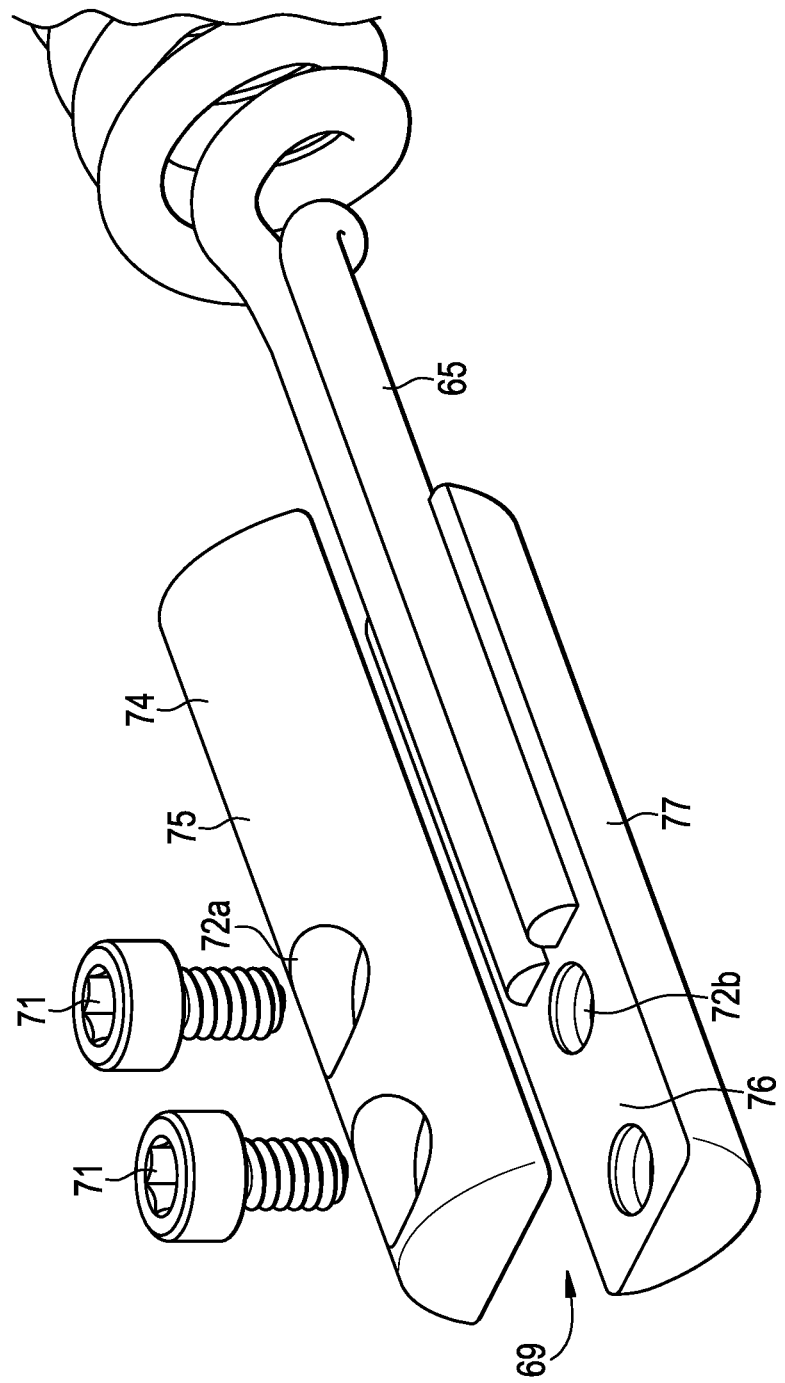
FIG. 11 discloses an embodiment in which a set screw locks semi-cylinder portions of an end rod.

Now referring to FIG. 11, in some embodiments, the spring terminates in a linear rod section 65 and mates with a rod end to clamp the spring in place.

Therefore, in accordance with the present invention, in one embodiment, each spring further comprises a first end 65 having a linear rod configuration, and the linear rod fits into a hollow bore (not shown) of the first end attachment feature 69.

In some embodiments, the first end attachment feature 69 comprises first 75 and second 77 semi-cylinders, and the device further comprises d) a set screw 71 passing through a first hole 72a in each of the outer surface 74 of the first semi-cylinder and a second hole 72b in the inner surface 76 of the second semi-cylinder.

Figure 12:
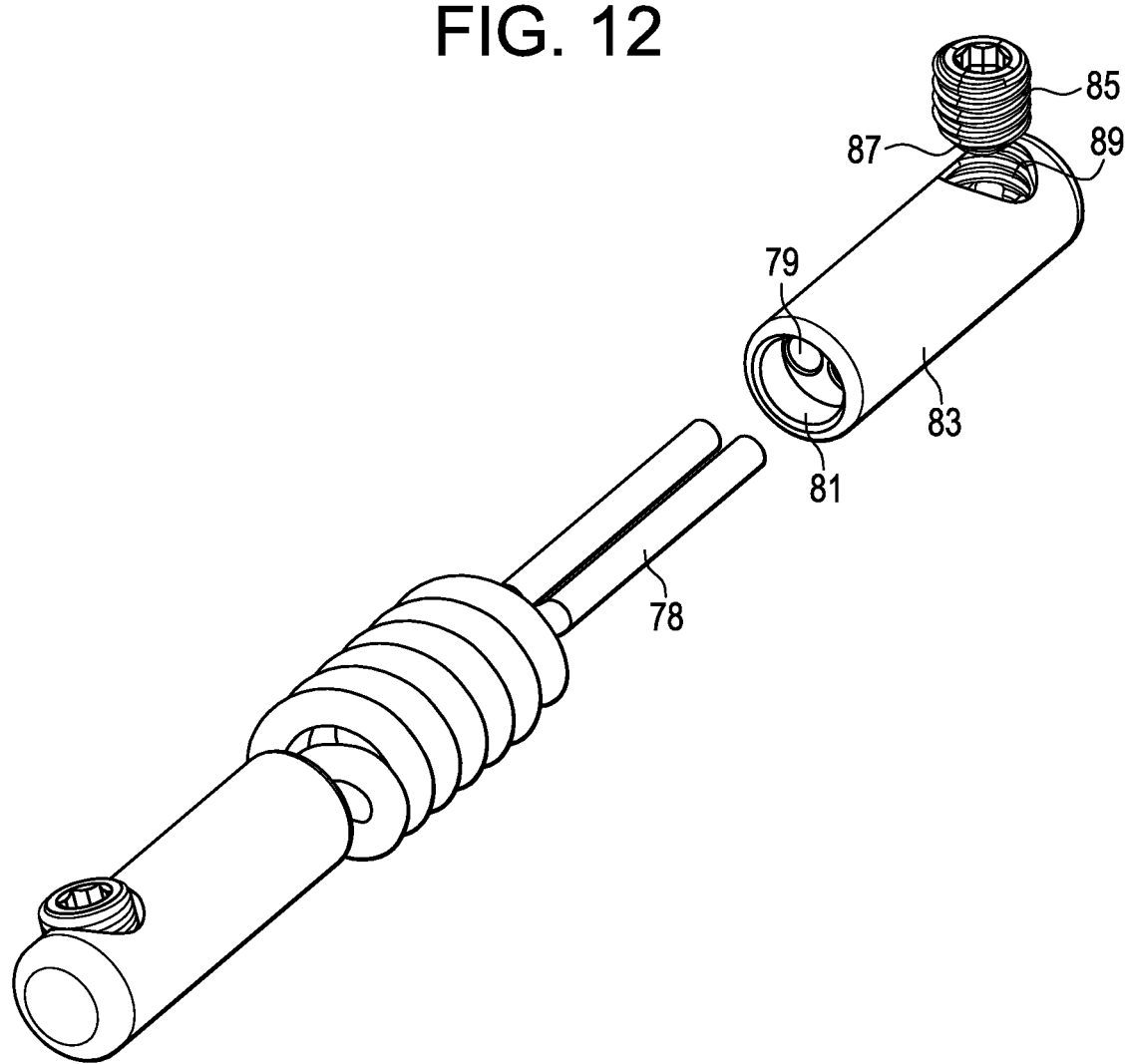
FIG. 12 discloses an embodiment in which the set screw locks the spring termination end into the hollow rod.

Now referring to FIG. 12, in some embodiments, a linear portion 78 of the terminating spring end mates with parallel bores 79 in the inner end 81 of the rod 83 that are aligned with the rod axis. A set screw 85 with a point 87 at its tip is passed through a transverse hole 89 in the body of the rod to spread the wires away from each other and lock the spring ends in place.

Also in accordance with the present invention, in one embodiment each spring further comprises a first end 78 having a linear rod configuration, wherein the linear rod fits into a hollow bore 79 in an inner end 81 of the first end attachment feature, and the device further comprises d) a set screw 85 passing through the first attachment feature to lock the linear rod. Preferably, an end of the set screw is frusto-conical.

Figure 13:
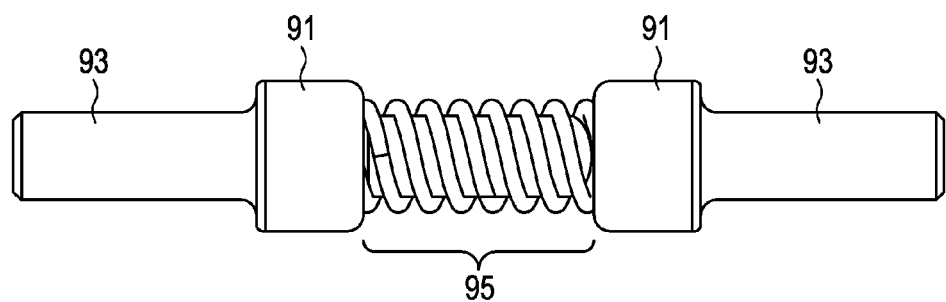
FIGS. 13 and 14 disclose side and cross-section views of a device having compression caps.
Figure 14:
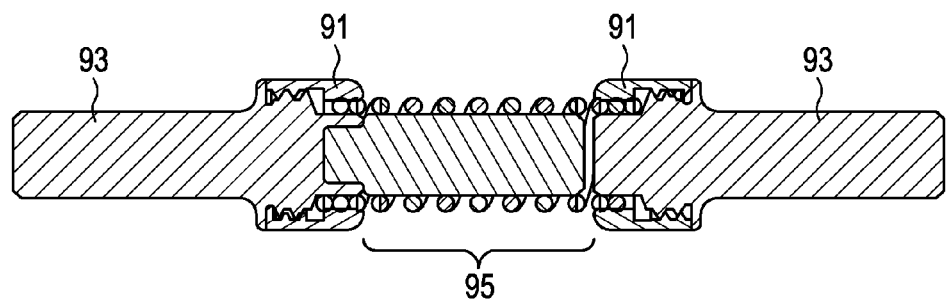

Now referring to FIGS. 13 and 14, the device may further include a compression assembly 91 (or compression cap) that has ends adapted to compress the spring unit. Tapered compression ends of the cap serve to clamp the dual spring in place.

Therefore, also in accordance with the present invention, in one embodiment the device further comprises: d) a compression cap 91 disposed between the first end attachment feature 93 and the intermediate spring portion 95.

Figure 15:
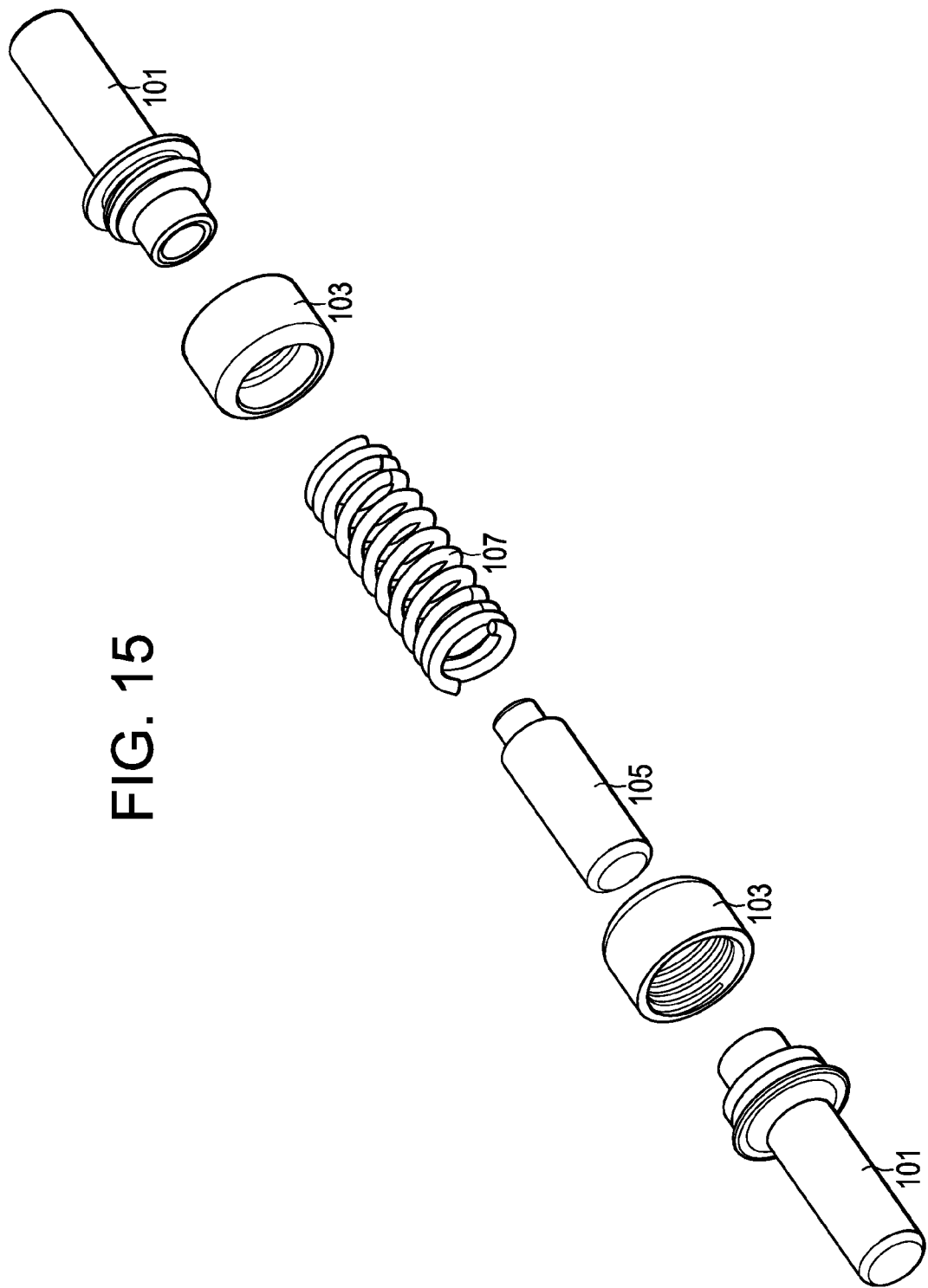
FIG. 15 discloses an exploded view of a device of the present invention in which the dual helix contains a polymer core and is flanked by a pair of compression caps.

FIG. 15 discloses an exploded view of a device of the present invention in which the dual helix contains a polymer core and is flanked by a pair of compression caps. Now referring to FIG. 15, there is provided an exploded view of FIGS. 13 and 14, showing rod ends 101, compression caps 103, a polymer core 105, and a spring 107.

The springs in the double helix may also terminate with a linear end section (not shown), which would allow smaller attachment rod ends to be used.

Figure 16A:
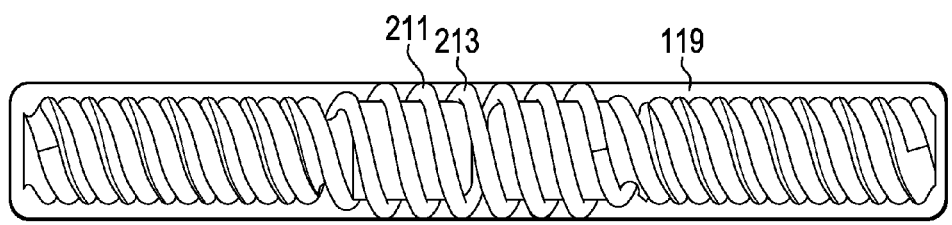
FIGS. 16a-c disclose various views of a preferred embodiment of the present invention containing an overmolded polymer component.
Figure 16B:
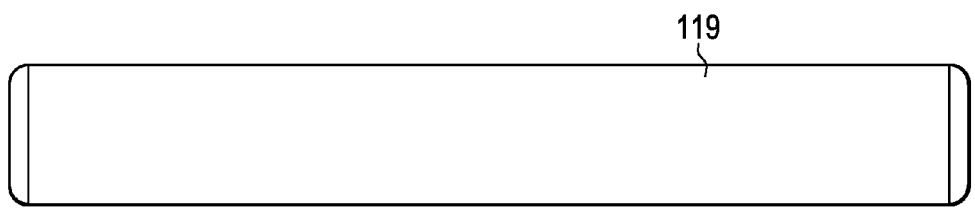
Figure 16C:
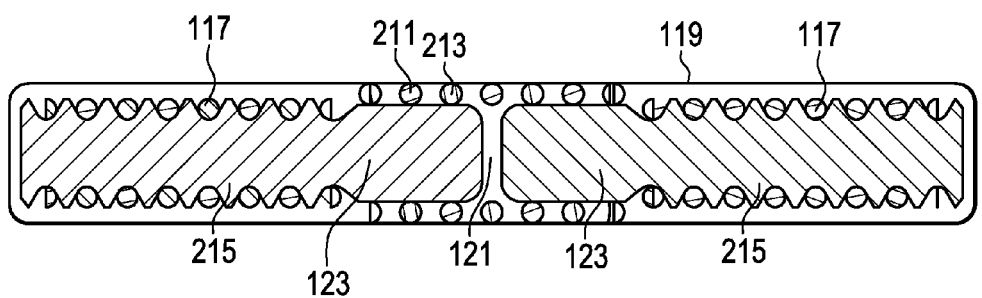

Now referring to FIGS. 16a-c, there is provided a device of the present invention constructed of five components:
  a) two springs 211,213 creating a double helix configuration,
  b) two threaded rod ends 215, which are threaded through the helical terminations 117 of the spring on each end, and
  c) a final overmold structure 119 that creates a constant diameter and clamping surface.

The two threaded rod ends could be made from any material and the split 121 in the center allows the spring to somewhat stretch. This split could be located anywhere along the core and have a variety of geometries. The threaded ends 115 of the rods 123 prevent compression of spring during clamping and provide attachment means for the spring. The overmold structure provides the device with a constant overall diameter.

Therefore, in preferred embodiments of the present invention, there is provided a PDS device having a dual lead coil spring design forming a double helix, where the spring wire has a circular cross section. This device achieves its axial stiffness primarily by way of the double helix spring and secondly by way of the polymer core component. Shear and bending forces are also mediated by the interaction between these components. This device will have relatively low resistance to axial displacements at low loads, but will become increasingly stiff as the double helix spring engages the polymer core component. Accordingly, there is provided a comprehensive dynamic stabilization system with different devices having different stiffnesses to serve a variety of patients' needs. This system may be particularly useful in multi-level cases, wherein the stiffnesses at adjacent flexible segments may vary.

One skilled in the art will appreciate that the rod of the device may be configured for use with any type of bone anchor, e.g., bone screw or hook; mono-axial or polyaxial. Typically, a bone anchor assembly includes a bone screw, such as a pedicle screw, having a proximal head and a distal bone-engaging portion, which may be an externally threaded screw shank. The bone screw assembly may also have a receiving member that is configured to receive and couple a spinal fixation element, such as a spinal rod or spinal plate, to the bone anchor assembly.

The receiving member may be coupled to the bone anchor in any well-known conventional manner. For example, the bone anchor assembly may be poly-axial, as in the present exemplary embodiment in which the bone anchor may be adjustable to multiple angles relative to the receiving member, or the bone anchor assembly may be mono-axial, e.g., the bone anchor is fixed relative to the receiving member. An exemplary poly-axial bone screw is described U.S. Pat. No. 5,672,176, the specification of which is incorporated herein by reference in its entirety. In mono-axial embodiments, the bone anchor and the receiving member may be coaxial or may be oriented at angle with respect to one another. In poly-axial embodiments, the bone anchor may biased to a particular angle or range of angles to provide a favored angle the bone anchor. Exemplary favored-angle bone screws are described in U.S. Patent Application Publication No. 2003/0055426 and U.S. Patent Application Publication No. 2002/0058942, the specifications of which are incorporated herein by reference in their entireties.

Therefore, in accordance with the present invention, there is provided a posterior dynamic spinal stabilization system for use in a human spine, comprising:
  a) first and second bone anchors, each anchor having a recess for receiving a rod,
  b) the device of the present invention.

Generally, in using the present invention, two bone anchors such as polyaxial screws are inserted into adjacent pedicles within a functional spinal unit of a patient. The cylinder-bumper-rod assembly of the present invention is then inserted into the patient between the anchors. The first hollow cylinder is attached to the first bone anchor by laying the outer annular surface of the first hollow cylinder into the first bone anchor recess and tightening an appropriate set screw. Similarly, the second end of the first rod is attached to the second bone anchor by laying the second end into the second bone anchor recess and tightening the appropriate set screw. More preferably, this is achieved in a minimally invasive surgery.

In some embodiments, at least one end of the cylinder-bumper-rod assembly has a bullet nose for ease of insertion.

In some embodiments, the assemble may be implanted in accordance with the minimally invasive techniques and instruments disclosed in U.S. Pat. No. 7,179,261; and US Patent Publication Nos. US2005/0131421; US2005/0131422; US 2005/0215999; US2006/0149291; US2005/0154389; US2007/0233097; and US2005/0192589, the specifications of which are hereby incorporated by reference in their entireties.

Therefore, in accordance with the present invention, there is provided a method of implanting a posterior dynamic spinal stabilization system, comprising the steps of:
  a) inserting two bone anchors into adjacent pedicles within a functional spinal unit of a patient, each bone anchor having a recess for receiving a rod,
  b) providing a polyaxial dynamic stabilization DEVICE comprising:

Each component of the design may be made from biocompatible, implantable materials known in the art such as stainless steel, titanium, nitinol, polyetheretherketone (PEEK) or alternative polyarylketones, carbon fiber reinforced polymers, and high performance elastomers such as silicones, dimethylsiloxanes, silicone-urethanes, polyether-urethanes, silicone-polyether-urethanes, polycarbonate urethanes, and silicone-polycarbonate-urethanes.

Preferably, the coil and rod components are titanium alloy (Ti-6Al-4V) or cobalt-chrome alloy (e.g. Co—Cr—Mo). If a cobalt-chrome alloy is selected, the alloy is preferably in a work-hardened condition so as to resist deformation upon securing to the bone anchor (e.g with a set screw). Preferably, the solid rod component is either titanium alloy or PEEK.

If a metal is chosen as a material of construction, then the metal is preferably selected from the group consisting of nitinol, titanium, titanium alloys (such as Ti-6Al-4V), cobalt-chrome alloys (such as CrCo or Cr—Co—Mo) and stainless steel.

If a polymer is chosen as a material of construction, then the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the core polymer and/or rod component is made from a composite comprising carbon fiber. Composites comprising carbon fiber are advantageous in that they typically have a strength and stiffness that is superior to neat polymer materials such as a polyarylethyl ketone PAEK. In some embodiments, the core is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:

a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

The elastomer core component is preferably made of a thermoplastic, biocompatible, high performance polycarbonate-urethance (PCU). The stiffness, or durometer of the PCU can be tailored to meet the specifications for the dynamic device. In preferred embodiments, the surface of the device components that will be attached to the elastomer are treated prior to attaching the bumper using known surface treatment methods such as surface roughening (e.g. grit blasting), chemical functionalization (e.g. primers), and plasma treatments know in the art. Alternatively or in conjunction with using a surface treatment, an adhesive may be used to enhance bonding, e.g. using cyanoacrylates. In one preferred embodiment, the surfaces of the device components that will attached to the elastomer will first be roughened using grit blasting, then chemically functionalized using primer, then the elastomer will be overmolded onto the device components.

We claim:

1. A posterior dynamic stabilization device comprising;
   i) first and second bone anchors,
   ii) a double helix spring comprising:
      a) a first end attachment feature attached to the first bone anchor and having an inner end having a hollow bore,
      b) a second end attachment feature attached to the second bone anchor and having an inner end having a hollow bore,
      c) an intermediate spring portion comprising first and second springs, each spring having a helical intermediate portion, the helical intermediate portions oriented to form a double helix,
wherein each spring comprises first and second linear ends extending from the helical intermediate portion,
wherein the first linear end of each spring is located in the hollow bore of the first end attachment feature, and the second linear end of each spring is located in the hollow bore of the second end attachment feature.

* * * * *